United States Patent
Liang et al.

(10) Patent No.: US 12,268,769 B2
(45) Date of Patent: Apr. 8, 2025

(54) HAIR COLORING COMPOSITIONS

(71) Applicant: L'OREAL, Paris (FR)

(72) Inventors: Jun Liang, Brooklyn, NY (US); Heather Yoonsoo Lee, Wayne, NJ (US)

(73) Assignee: L'OREAL, Paris (FR)

(*) Notice: Subject to any disclaimer, the term of this patent is extended or adjusted under 35 U.S.C. 154(b) by 40 days.

(21) Appl. No.: 18/455,869

(22) Filed: Aug. 25, 2023

(65) Prior Publication Data

US 2024/0148629 A1 May 9, 2024

Related U.S. Application Data

(60) Provisional application No. 63/373,608, filed on Aug. 26, 2022.

(30) Foreign Application Priority Data

Oct. 19, 2022 (FR) ..................... 2210811

(51) Int. Cl.
| | | |
|---|---|---|
| *A61Q 5/10* | (2006.01) | |
| *A61K 8/49* | (2006.01) | |
| *A61Q 5/06* | (2006.01) | |

(52) U.S. Cl.
CPC ............ *A61K 8/4973* (2013.01); *A61Q 5/065* (2013.01); *A61K 2800/4322* (2013.01); *A61K 2800/5426* (2013.01); *A61K 2800/80* (2013.01)

(58) Field of Classification Search
CPC .......... A61K 8/4973; A61K 2800/4322; A61K 2800/5426; A61K 2800/80; A61K 8/342; A61K 8/345; A61K 8/416; A61Q 5/065
USPC .......................................................... 8/405
See application file for complete search history.

(56) References Cited

U.S. PATENT DOCUMENTS

| | | |
|---|---|---|
| 4,859,456 A | 8/1989 | Marschner |
| 5,362,494 A | 11/1994 | Zysman et al. |
| 5,961,668 A * | 10/1999 | Akram ............ A61Q 5/10 |
| | | 8/618 |
| 6,620,409 B2 | 9/2003 | Bossmann et al. |
| 6,656,458 B1 | 12/2003 | Philippe et al. |
| 9,187,717 B2 | 11/2015 | Torres et al. |
| 10,470,984 B2 | 11/2019 | Ilekti et al. |
| 11,260,000 B2 | 3/2022 | Ikeda et al. |
| 11,337,906 B2 | 5/2022 | Lee et al. |
| 2008/0299168 A1 | 12/2008 | Dadey et al. |
| 2012/0255130 A1 | 10/2012 | Bazito et al. |
| 2013/0064871 A1 | 3/2013 | Richard et al. |
| 2017/0112753 A1 | 4/2017 | Douezan et al. |
| 2017/0239157 A1 | 8/2017 | Jager Lezer et al. |
| 2017/0246099 A1 | 8/2017 | Jager Lezer et al. |
| 2021/0059915 A1 | 3/2021 | Liang |
| 2021/0299011 A1 | 9/2021 | Park |

FOREIGN PATENT DOCUMENTS

| | | | |
|---|---|---|---|
| CN | 104220535 B | 3/2017 | |
| GB | 1291843 A * | 10/1972 | ............ A61Q 9/00 |
| JP | 6535592 B2 | 6/2019 | |
| KR | 20100081509 A | 7/2010 | |
| WO | 03037281 A1 | 5/2003 | |
| WO | 2010078985 A3 | 3/2011 | |
| WO | 2018178341 A1 | 10/2018 | |

OTHER PUBLICATIONS

STIC Search Report dated Nov. 13, 2024.*
Preliminary Search Report and Written Opinion issued on May 4, 2023 for corresponding French Application No. FR2210811.
Database GNPD [Online]; MINTEL; Anonymous: "Darken and Strengthen Shampoo," 2021 XP093043876.

* cited by examiner

*Primary Examiner* — Eisa B Elhilo
(74) *Attorney, Agent, or Firm* — POLSINELLI PC

(57) ABSTRACT

The present disclosure relates to hair coloring compositions and methods for coloring hair. The hair coloring compositions include: (a) one or more hair colorants; (b) one or more ketal/acetal of glycerin compounds of Formula (I); (c) one or more cationic surfactants; (d) one of more fatty alcohols having at least 8 carbon atoms; (e) one or more polyols having from 2 to 10 carbon atoms; and (f) less than 5 wt. %, based on the total weight of the composition, of water and monoalcohols having from 1 to 6 carbon atoms. The hair coloring compositions are preferably solubilized, non-emulsified compositions.

20 Claims, No Drawings

HAIR COLORING COMPOSITIONS

CROSS-REFERENCE TO RELATED APPLICATIONS

This application claims the benefit of U.S. Ser. No. 63/373,608, filed Aug. 26, 2022, and the benefit of French Application No. FR 2210811, filed on Oct. 19, 2022, which are incorporated herein by reference in their entirety.

FIELD OF THE DISCLOSURE

The present disclosure relates to hair coloring compositions, and to methods for coloring hair with the compositions.

BACKGROUND

There are many methods and products available for changing the natural color of hair. Semi-permanent or temporary dyeing methods, or direct dyeing methods, temporarily change the color of hair. These methods can change the color of the hair to varying degrees and the color change may withstand several rounds of shampooing. Many consumers seek more permanent results, and therefore default to oxidative dye products that contain hydrogen peroxide or other oxidants. To provide the consumer with the shade, longevity, and the intensity of color desired, an oxidative coloring process is utilized. Permanent hair dyeing formulations typically include primary intermediates (also known as oxidative hair dye precursors) and couplers (also known as color modifiers or secondary intermediates). These dye precursors are sufficiently small, polar and soluble to diffuse into the hair shaft where, once activated by an oxidizing agent under basic conditions, such as hydrogen peroxide, the primary intermediates react with other dye precursors, e.g., couplers, to form larger colored chromophores in the hair shaft. The chromophores formed in the hair shaft do not readily diffuse from the hair during subsequent washing.

The oxidative coloring of hair can require long processing times. For instance, oxidative coloring processes involve premixing a coloring base and a developer. This mixture is then applied to the hair and must remain on the hair for a long period of time (an extended "processing" time) to potentiate the desired color change. Direct dyes, however, do not require admixing and activation by oxidizing agents and do not require long processing times.

Many attempts have been made by the hair color industry to enhance the washfastness (tenacity) of direct dyes by either forming a covalent bond between chromophore and proteins inside hair or increasing the number of binding sites, typically cationic centers, on the chromophore. However, each attempt has its drawbacks.

The approach through covalent bonding does not differentiate proteins in hair from skin. The approach through multiple binding sites on the dyes (i.e. multiple positive charges to interact with negative sites on hair, either by bonding several monocationic dyes together or by installing multiple cationic centers on a single chromophore) runs into the obstacles of uneven color due to uneven damage (negative charges) along the length of the hair fibers and reduced dye penetration into hair fibers because the dyes are typically at least twice as large as common oxidative dye precursors.

An increase in the number of binding sites minimizes bleeding and color loss caused by rinsing by providing stronger hair-chromophore interactions. However, the same strong binding force to the cuticle also prevents the chromophores from penetrating deep into the cortex of hair, because it is difficult for dyes with multiple positive charges to diffuse through negatively charged networks of keratin proteins.

Additionally, since polycationic dyes remain bound to the hair surface rather than penetrating into the fiber, it is difficult to produce dark shades, due to limited binding sites on the surface of hair.

SUMMARY OF THE DISCLOSURE

The instant disclosure relates to hair coloring compositions and to methods for coloring the hair using the compositions. Upon application to wet or damp hair, the compositions preferably form a lamellar phase, which surprisingly enhances the deposition of colorants (e.g., direct dyes and oxidative dyes) and conditioning active agents (such as cationic surfactants and fatty compounds) onto the hair. The enhanced deposition of colorants improves the coloring of hair while the enhanced deposition of conditioning active agents provides a smoothing and softening effect to the hair. The result is vibrantly colored hair having a shiny and nourished appearance. The coloring compositions typically include:

(a) one or more hair colorants selected from direct dyes, oxidative dye precursors, couplers, and a combination thereof;

(b) one or more ketal/acetal of glycerin compounds of Formula (I):

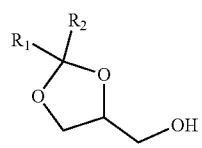

wherein $R_1$ and $R_2$ can be the same or different and are independently selected from hydrogen, $C_1$-$C_6$ alkyl, $C_1$-$C_6$ alkenyl, $C_1$-$C_6$ heteroalkyl, $C_1$-$C_6$ heteroalkenyl, aryl, heteroaryl, $C_3$-$C_6$ cycloalkyl, $C_3$-$C_6$ hetero ($C_3$-$C_6$)cycloalkyl, aryl, heteroaryl, optionally substituted; or $R_1$ and $R_2$ may together form a $C_3$-$C_6$ cycloalkyl, $C_3$-$C_6$ heterocycloalkyl, aryl, or heteroaryl, optionally, substituted;

wherein heteroatoms are selected from N, O or S;

(c) one or more cationic surfactants;

(d) one of more fatty alcohols having at least 8 carbon atoms;

(e) one or more polyols having from 2 to 10 carbon atoms;

(f) less than 5 wt. % of water and monoalcohols having from 1 to 6 carbon atoms;

wherein all weight percentages are based on a total weight of the composition.

The composition is typically a solubilized, non-emulsified composition. Upon application to wet or damp hair, the composition preferably forms a lamellar phase in situ. In various embodiments, the composition may have an opaque appearance upon application to the hair.

Nonlimiting examples of direct dyes include nitro-phenylenediamines, nitro-aminophenols, azo dyes, anthraquinones, triarylmethane dyes, indophenols, and a combination thereof. Nonlimiting examples of oxidative dye precursors include ortho aminophenols, para aminophenols, ortho phenylenediamines, para phenylenediamines, double bases, heterocyclic bases, m-aminophenol, 2,4-diaminophenoxyethanol hcl, toluene-2,5-diamine thioglycerin, p-aminophenol, 2-amino-3 hydroxypyridine, 4-amino-2-hydroxytoluene, acid addition salts thereof, and a combination thereof. Nonlimiting examples of couplers include meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid, and a combination thereof.

In various embodiments, one or more ketal/acetal of glycerin compounds of formula (I) are selected from compounds having at least one of $R_1$ and $R_2$ being a linear, branched, or cyclic $C_1$-$C_6$ alkyl. Preferably, $R_1$ and $R_2$ are independently a linear $C_1$-$C_6$ alkyl, for example isopropylidene glycerol.

Nonlimiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and combinations thereof.

The polyols preferably have two or three hydroxyl groups. Nonlimiting examples of include ethylene glycol, propylene glycol, butylene glycol, hexylene glycol, pentylene glycol, 1,3-propanediol, diethylene glycol, dipropylene glycol, caprylyl glycol, glycerin, and a combination thereof.

Nonlimiting examples of useful fatty alcohols include linear or branched fatty alcohols having from 10 to 30 carbon atoms, preferably from 12 to 28 carbon atoms. In various embodiments, the fatty alcohols are selected from capryl alcohol, pelargonic alcohol, decyl alcohol, undecyl alcohol, lauryl alcohol, tridecyl alcohol, myristyl alcohol, pentadecyl alcohol, cetyl alcohol, palmitoleyl alcohol, isostearyl alcohol, isocetyl alcohol, heptadecyl alcohol, stearyl alcohol, cetearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, and myricyl alcohol.

Nonlimiting examples of polyols having from 2 to 10 carbon atoms include ethylene glycol, propylene glycol, butylene glycol, hexylene glycol, pentylene glycol, 1,3-propanediol, diethylene glycol, dipropylene glycol, caprylyl glycol, and glycerin.

In various embodiments, the compositions include one or more emollients. For example, the one or more emollients may be selected from fatty esters, fatty ethers, propylene glycol fatty acid esters, fatty carbonates, and combinations thereof.

In various embodiments, the compositions include one or more thickening polymers. For example, the one or more thickening polymers nonionic thickening polymers, cationic thickening polymers, and a combination thereof. Nonlimiting examples of nonionic thickening polymers include, and a combination thereof. For example, the cationic thickening polymers may be a cationic thickening polymer comprising a quaternary amine group or a quaternary ammonium group. Nonlimiting examples include polyquaternium-10, polyquaternium-67, and a combination thereof.

In certain embodiments, the composition optionally includes one or more fatty acids. Nonlimiting examples of fatty acids include caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof. In various embodiments, the one or more fatty acids are selected from non-linear fatty acids (unsaturated fatty acids and/or branched fatty acids), preferably mono-unsaturated fatty acids and/or branched fatty acids.

The hair coloring compositions are useful in methods for coloring hair, and methods for conditioning and/or styling hair. The compositions can be applied immediately after shampooing the hair. The compositions can also be applied on hair immediately after shampooing and conditioning the hair. The hair coloring compositions can also be applied to the hair before shampooing. In various embodiments, the hair coloring compositions are applied to the hair, allowed to remain on the hair for a period, and optionally rinsed (or shampooed) from the hair. After treatment, the hair can be dried and styled as desired. In other embodiments, the hair coloring compositions are applied as a leave-on product. For example, the compositions can be applied to wet or damp hair and allowed to remain on the hair indefinitely, i.e., the hair composition is not removed or rinsed from the hair prior to styling the hair.

DETAILED DESCRIPTION OF THE DISCLOSURE

The instant disclosure relates to hair coloring compositions and to methods for coloring the hair using the compositions. Upon application to wet or damp hair, the compositions preferably form a lamellar phase, which surprisingly enhances the deposition of colorants (e.g., direct dyes and oxidative dyes) and conditioning active agents (such as cationic surfactants and fatty compounds) onto the hair. The enhanced deposition of colorants improves the coloring of hair while the enhanced deposition of conditioning active agents provides a smoothing and softening effect to the hair. The result is vibrantly colored hair having a shiny and nourished appearance. The coloring compositions typically include:
  (a) one or more hair colorants selected from direct dyes, oxidative dye precursors, couplers, and a combination thereof;
  (b) one or more ketal/acetal of glycerin compounds of Formula (I):

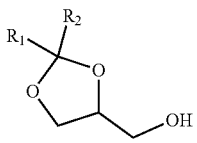

(I)

wherein $R_1$ and $R_2$ can be the same or different and are independently selected from hydrogen, $C_1$-$C_6$ alkyl, $C_1$-$C_6$ alkenyl, $C_1$-$C_6$ heteroalkyl, $C_1$-$C_6$ heteroalkenyl, aryl, heteroaryl, $C_3$-$C_6$ cycloalkyl, $C_3$-$C_6$ hetero ($C_3$-$C_6$)cycloalkyl, aryl, heteroaryl, optionally substituted; or $R_1$ and $R_2$ may together form a $C_3$-$C_6$ cycloalkyl, $C_3$-$C_6$ heterocycloalkyl, aryl, or heteroaryl, optionally, substituted;

wherein heteroatoms are selected from N, O or S;

(c) one or more cationic surfactants;

(d) one of more fatty alcohols having at least 8 carbon atoms;

(e) one or more polyols having from 2 to 10 carbon atoms;

(f) less than 5 wt. % of water and monoalcohols having from 1 to 6 carbon atoms;

wherein all weight percentages are based on a total weight of the composition.

The compositions are typically solubilized (not emulsified) until applied to a wet or damp substrate, e.g., hair. The compositions may be transparent or translucent. Upon application to the wet or damp substrate, the compositions for a lamellar phase in situ. In various embodiments, upon application to the wet or damp substrate, the compositions form an opaque appearance. Furthermore, (a) Hair Colorants A "hair colorant" (interchangeable with "hair coloring agent") is a compound or ingredient included in compositions to intentionally change the color of hair. Nonlimiting examples of hair coloring agents include direct dyes, oxidative dye precursors, couplers, bleaching agents (e.g., peroxides such as hydrogen peroxide), etc. Nonlimiting examples of "hair colorants" include direct dyes, oxidative dye precursors, couplers, and a combination thereof. Preferably, the one or more hair coloring agents includes at least one direct dye.

Nonlimiting examples of direct dyes include nitro-phenylenediamines, nitro-aminophenols, azo dyes, anthraquinones, triarylmethane dyes, indophenols, and a combination thereof. Nonlimiting examples of oxidative dye precursors include ortho aminophenols, para aminophenols, ortho phenylenediamines, para phenylenediamines, double bases, heterocyclic bases, m-aminophenol, 2,4-diaminophenoxyethanol hcl, toluene-2,5-diamine thioglycerin, p-aminophenol, 2-amino-3 hydroxypyridine, 4-amino-2-hydroxytoluene, acid addition salts thereof, and a combination thereof. Nonlimiting examples of couplers include meta-aminophenols, meta-phenylenediamines and meta-diphenols, naphthols, mono- or polyhydroxylated naphthalene derivatives, heterocyclic couplers, acid addition salts thereof, and a combination thereof.

In various embodiments, the one or more direct dyes are selected from cationic dyes, anionic dyes, and a combination thereof. In a preferred embodiment, at least one of the one or more direct dyes is selected from anionic dyes.

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2 (Ext Violet 2), D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

A more exhaustive but nonlimiting list of useful direct dyes is included under the heading "Direct Dyes."

The hair coloring compositions may include at least one oxidative dye precursor. The oxidative dye precursor of the present disclosure may be selected from any type of oxidative dye precursor useful for imparting color to hair. The oxidative dye precursor may also encompass a wide variety of oxidation dye precursors. These include primary dye intermediates and couplers.

Nonlimiting examples of primary dye intermediates include ortho or para aminophenols, ortho or para phenylenediamines, double bases, heterocyclic bases, and the acid addition salts thereof.

Nonlimiting examples of couplers include meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d] oxazole derivatives, pyrazolo[3,4-d]thiazole derivatives, thiazoloazole S-oxide derivatives, thiazoloazole S,S-dioxide derivatives, and the acid addition salts thereof.

A more exhaustive but nonlimiting list of useful oxidation dye precursors and couplers is included under the heading "Oxidative Dye Precursors and Couplers."

The amount of the one or more hair colorants included in the composition is an amount sufficient to impart a desired color to the hair. Those skilled in the art can determine appropriate amounts of hair colorants needed depending on, for example, the type of hair colorant included in the compositions (e.g., direct dye, oxidative dye precursor, couplers, etc.), the desired degree of color change to the hair, and the other ingredients included in the compositions. Nonetheless, in various embodiments, the total amount of the one or more hair colorants is from about 0.001 to about 5 wt. %, based on the total weight of the hair coloring composition. In further embodiments, the total amount of the one or more hair colorants is from about 0.001 to about 3 wt. %, about 0.001 to about 2 wt. %, about 0.01 to about 5 wt. %, about 0.01 to about 3 wt. %, about 0.01 to about 2 wt. %, about 0.1 to about 5 wt. %, about 0.1 to about 3 wt. %, or about 0.1 to about 1 wt. %, including ranges and sub-ranges therebetween, based on the total weight of the composition.

(b) Ketal/Acetal of Glycerin Compounds of Formula (I)

The hair coloring compositions of the instant disclosure include one or more ketal/acetal of glycerin compounds of formula (I):

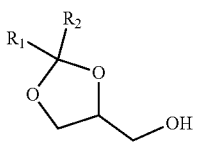

(I)

wherein
$R_1$ and $R_2$ can be the same or different and are independently selected from hydrogen, $C_1$-$C_6$ alkyl, $C_1$-$C_6$ alkenyl, $C_1$-$C_6$ heteroalkyl, $C_1$-$C_6$ heteroalkenyl, aryl, heteroaryl, $C_3$-$C_6$ cycloalkyl, $C_3$-$C_6$ heterocycloalkyl, optionally substituted; or
$R_1$ and $R_2$ may together form a $C_3$-$C_6$ cycloalkyl, $C_3$-$C_6$ heterocycloalkyl, aryl, or heteroaryl, optionally substituted;
wherein heteroatoms are selected from N, O or S.

As used herein, the term "alkyl" is given its ordinary meaning in the art and includes saturated aliphatic groups, including straight-chain alkyl groups and branched-chain alkyl groups.

As used herein, the term "cycloalkyl" is given its ordinary meaning in the art and includes an alkyl as defined above but forming a ring having 3 to 6 carbon atoms.

As used herein, "alkenyl" is given its ordinary meaning in the art and includes straight chain and branched chain hydrocarbon groups containing at least one carbon-carbon double bond.

The term "heteroalkyl" is given its ordinary meaning in the art and includes an alkyl as described herein except that one or more atoms is a heteroatom (e.g., oxygen, nitrogen, sulfur, and the like).

As used herein, the term "heterocycloalkyl" is given its ordinary meaning in the art and includes a heteroalkyl as discussed above except in the form of a ring having 3 to 6 carbon atoms in which one or more atoms is a heteroatom (e.g., oxygen, nitrogen, sulfur, and the like).

As used herein, the term "heteroalkenyl" is given its ordinary meaning in the art and includes straight chain and branched chain hydrocarbon groups containing at least one carbon-carbon double bond and in which one or more atoms is a heteroatom (e.g., oxygen, nitrogen, sulfur, and the like).

As used herein, the term "aryl" is given its ordinary meaning in the art and includes aromatic carbocyclic groups having a single ring (e.g., phenyl) or multiple rings (e.g., biphenyl).

As used herein, the term "heteroaryl" is given its ordinary meaning in the art and includes aryl groups as described above except that one or more atoms is a heteroatom (e.g., oxygen, nitrogen, sulfur, and the like), optionally substituted.

The alkyl, alkenyl, heteroalkyl, heteraokenyl, aryl, heteroaryl, cycloalkyl, heterocycloalkyl groups discussed above may be optionally substituted, For example, optionally substituted with an alkyl, alkenyl, alkynyl, cycloalkyl, cycloalkenyl, cycloalkynyl, aryl, alkaryl, aralkyl, optionally interrupted or terminated by heteroatoms, carbonyl groups, cyano, $NO_2$, alkoxy, aryloxy, hydroxy, amino, thioalkyl, thioaryl, sulfur-containing groups, halides, substituted derivatives thereof, and the like.

In a preferred embodiment at least one of $R_1$ and $R_2$ is a linear, branched, or cyclic $C_1$-$C_6$ alkyl, preferably a linear or branched $C_1$-$C_6$ alkyl. In a further preferred embodiment, both $R_1$ and $R_2$ are both a linear, branched, or cyclic $C_1$-$C_6$ alkyl, preferably both a linear or branched $C_1$-$C_6$ alkyl.

Nonlimiting examples of ketal/acetal of glycerin compounds of formula (I) include isopropylidene glycerol (2,2-dimethyl-1,3-dioxolane-4-methanol), (2,2-diethyl-1,3-dioxolan-4-yl)methanol, (2,2-dipropyl-1,3-dioxolan-4-yl) methanol, ((2-methyl-1,3-dioxolan-4-yl)methanol), (2-ethyl-1,3-dioxolan-4-yl)methanol, (2-propyl-1,3-dioxolan-4-yl)methanol, glycerol formal (4-hydroxymethyl-1,3-dioxolane), 2-isobutyl-2-methyl-1,3-dioxolane-4-methanol, 2-phenyl-1,3-dioxolane-4-methanol, and a combination thereof. Most preferably, the one or more ketal/acetal of glycerin is isopropylidene glycerol (2,2-dimethyl-1,3-dioxolane-4-methanol).

As used herein, the term "isopropylidene glycerol" is 2,2-dimethyl-1,3-dioxolane-4-methanol, also known as "Solketal," has the following formula:

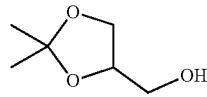

Isopropylidene glycerol
(2,2-dimethyl-1,3-dioxane-4-methanol)

The total amount of the one or more ketal/acetal of glycerin compounds of formula (I) will vary. Nonetheless, in various embodiments, the total amount of the one or more ketal/acetal of glycerin compounds of formula (I) is from about 5 to about 95 wt. %, based on the total weight of the composition. In further embodiments, the total amount of the one or more ketal/acetal of glycerin compounds of formula (I) is from about 5 to about 90 wt. %, about 5 to about 80 wt. %, about 5 to about 70 wt. %, about 5 to about 60 wt. %, about 5 to about 50 wt. %, about 5 to about 40 wt. %, including ranges and sub-ranges therebetween, based on the total weight of the composition.

In certain embodiments, the total amount of the one or more ketal/acetal of glycerin compounds of formula (I) is from about is from about 10 to about 95 wt. %, about 20 to about 95 wt. %, about 30 to about 95 wt. %, about 40 to about 95 wt. %, about 50 to about 95 wt. %, about 60 to about 95 wt. %, about 70 to about 95 wt. %, about 10 to about 90 wt. %, about 20 to about 90 wt. %, about 30 to about 90 wt. %, about 40 to about 90 wt. %, about 50 to about 90 wt. %, about 60 to about 90 wt. %, or about 70 to about 95 wt. %, including ranges and sub-ranges therebetween, based on the total weight of the composition.

In preferred embodiments, the total amount of the one or more ketal/acetal of glycerin compounds of formula (I) is from about 5 to about 40 wt. %, about 5 to about 35 wt. %, about 5 to about 30 wt. %, about 5 to about 25 wt. %, about 10 to about 40 wt. %, about 10 to about 35 wt. %, about 10 to about 30 wt. %, about 10 to about 25 wt. %, about 15 to about 40 wt. %, about 15 to about 35 wt. %, about 15 to about 30 wt. %, or about 15 to about 25 wt. %, including ranges and sub-ranges therebetween, based on the total weight of the composition.

(c) Cationic Surfactants

The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and a combination thereof.

In various embodiments, the one or more cationic surfactants are preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a combination thereof.

In further embodiments, the one or more cationic surfactants are preferably selected from cetrimonium chloride, behentrimonium chloride, behentrimonium methosulfate, stearamidopropyl dimethylamine, and a combination thereof.

A more exhaustive but nonlimiting list of useful cationic surfactants is provided later, under the heading "Cationic Surfactants."

The total amount of the one or more cationic surfactants in the hair coloring compositions will vary. Nonetheless, in various embodiments, the total amount of the one or more cationic surfactants is from about 0.1 to about 10 wt. %, based on the total weight of the composition. In further embodiments, the total amount of the one or more cationic surfactants is from about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, about 0.5 to about 3 wt. %, about 1 to about 10 wt. %, about 1 to about 8 wt. %, about 1 to about 5 wt. %, or about 1 to about 3 wt. %, including ranges and sub-ranges therebetween, based on the total weight of the composition.

(d) Fatty Alcohols Having at Least 8 Carbon Atoms

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In various embodiments, the compositions include at least one solid fatty alcohol. Solid fatty alcohols are fatty alcohols that are solid at ambient temperature and at atmospheric pressure (25° C., 780 mmHg), and are insoluble in water, that is to say they have a water solubility of less than 1% by weight, preferably less than 0.5% by weight, at 25° C., 1 atm. The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms. Nonlimiting examples include lauryl alcohol (1-dodecanol); myristyl alcohol (1-tetradecanol), cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol), myricylic alcohol (1-triacontanol), and combinations thereof. In a preferred embodiment, the compositions include at least one solid fatty alcohol selected from myristyl alcohol, cetyl alcohol, stearyl alcohol, behenyl alcohol and combinations thereof such as cetylstearyl or cetearyl alcohol.

In various embodiments, the compositions include at least one liquid fatty alcohol, in particular containing C10-C34 and preferably have branched carbon chains and/or have one or more, preferably 1 to 3 double bonds. They are preferably branched and/or unsaturated (C=C double bond) and contain from 12 to 40 carbon atoms. The liquid fatty alcohols may be represented by: R—OH, wherein R denotes a C12-C24 branched or straight alkyl group or an alkenyl group, R being optionally substituted by one or more hydroxy groups. In certain embodiments, the liquid fatty alcohols are selected from branched saturated alcohols. Preferably, R does not contain a hydroxyl group. Nonlimiting examples include oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and combinations thereof. In other embodiments, the compositions are free or essentially free from liquid fatty alcohols, including the liquid fatty alcohols referenced above.

In a preferred embodiment, the one or more fatty alcohols are linear (straight chain) saturated fatty alcohols having from 10 to 30 carbon atoms, preferably from 12 to 28 carbon atoms, more preferably from 14 to 24 carbon atoms. Nonlimiting examples include decyl alcohol, undecyl alcohol, dodecyl alcohol, myristyl alcohol, cetyl alcohol, stearyl alcohol, cetearyl alcohol, behenyl alcohol, myricyl alcohol and a combination thereof.

The total amount of the one or more fatty alcohols in the hair coloring composition will vary. Nonetheless, in various embodiments, the total amount of the one or more fatty alcohols is from about 0.1 to about 10 wt. %, based on the total weight of the composition. In further embodiments, the total amount of the one or more fatty alcohols is from about 0.1 to about 8 wt. %, about 0.1 to about 5 wt. %, about 0.1 to about 4 wt. %, about 0.1 to about 3 wt. %, about 0.5 to about 10 wt. %, about 0.5 to about 8 wt. %, about 0.5 to about 5 wt. %, about 0.5 to about 4 wt. %, about 0.5 to about 3 wt. %, about 1 to about 10 wt. %, about 1 to about 8 wt. %, about 1 to about 5 wt. %, about 1 to about 4 wt. %, or about 1 to about 3 wt. %, including ranges and sub-ranges therebetween, based on the total weight of the composition.

(e) Polyols Having from 2 to 10 Carbon Atoms

The polyols have from 2 to 10 carbon atoms. Preferably the polyols also have two or three hydroxyl groups. For example, the polyols can be selected from glycols and glycerol. Nonlimiting examples of polyols having from 2 to 10 carbon atoms include ethylene glycol, propylene glycol, butylene glycol, hexylene glycol, pentylene glycol, 1,3-propanediol, diethylene glycol, dipropylene glycol, caprylyl glycol, and glycerin.

The total amount of the one or more polyols having from 2 to 10 carbon atoms will vary. In various embodiments, the total amount of the one or more polyols having from 2 to 10 carbon atoms is from about 5 to about 90 wt. %, based on the total weight of the compositions. In further embodiments, the total amount of the one or more polyols having from 2 to 10 carbon atoms is from about 10 to about 90 wt. %, about 15 to about 90 wt. %, about 20 to about 90 wt. %, about 5 to about 85 wt. %, about 10 to about 85 wt. %, about 15 to about 85 wt. %, about 20 to about 85 wt. %, about 5 to about 80 wt. %, about 10 to about 80 wt. %, about 15 to about 80 wt. %, about 20 to about 80 wt. %, about 5 to about 70 wt. %, about 10 to about 70 wt. %, about 15 to about 70 wt. %, about 20 to about 70 wt. %, about 5 to about 60 wt. %, about 10 to about 60 wt. %, about 15 to about 60 wt. %, about 20 to about 60 wt. %, about 5 to about 50 wt. %, about 10 to about 50 wt. %, about 15 to about 50 wt. %, or about 20 to about 50 wt. %, including ranges and sub-ranges therebetween, based on the total weight of the composition In preferred embodiments, the total amount of the one or more polyols having from 2 to 10 carbon atoms is from about 20 to about 85 wt. %, based on the total weight of the compositions. In further embodiments, the total amount of the one or more polyols having from 2 to 10 carbon atoms is from about 30 to about 85 wt. %, about 35 to about 85 wt. %, about 40 to about 85 wt. %, about 45 to about 85 wt. %, about 50 to about 85 wt. %, about 55 to about 85 wt. %, about 60 to about 85 wt. %, about 65 to about 85 wt. %, from about 30 to about 80 wt. %, about 35 to about 80 wt. %, about 40 to about 80 wt. %, about 45 to about 80 wt. %, about 50 to about 80 wt. %, about 55 to about 80 wt. %, about 60 to about 80 wt. %, or about 65 to about 80 wt. %, including ranges and sub-ranges therebetween, based on the total weight of the compositions.

In a preferred embodiment, the total amount of the one or more polyols having from 2 to 10 carbon atoms is greater than the total amount of the ketal/acetal of glycerin compounds of Formula (I).

Weight Ratio of (b) to (e)

In various embodiments, the one or more ketal/acetal of glycerin compounds of formula (I) of (b) and the one or more polyols having from 2 to 10 carbon atoms (e) are in a weight ratio of about 1:20 to about 20:1, about 1:15 to about 15:1, about 1:10 to about 10:1 ((b):(e)). In further embodiments, the the one or more ketal/acetal of glycerin compounds of formula (I) of (b) and the one or more polyols having from 2 to 10 carbon atoms (e) are in a weight ratio of about 1:1 to about 1:10 ((b):(e)). In further embodiments, the weight ratio of (b) to (e) is about 1:1 to about 1:8, about 1:1 to about 1:6, about 1:1 to about 1:5, about 1:1 to about 1:4, greater than 1:1 to about 1:10 greater than 1:1 to about 1:8, greater than 1:1 to about 1:6, greater than 1:1 to about 1:4, about 1:2 to about 1:10, about 1:2 to about 1:8, about 1:2 to about 1:6, about 1:2 to about 1:5, about 1:2 to about 1:4, about 1:3 to about 1:10, about 1:3 to about 1:8, about 1:3 to about 1:6, about 1:3 to about 1:5, or about 1:3 to about 1:4 ((b):(e)).

(f) Water and Monoalcohols

The compositions of the instant disclosure include very little water and monoalcohols having from 1 to 6 carbon atoms, preferably less than 5 wt. % of water and monoalcohols having from 1 to 6 carbon atoms. In some instances, the composition of the instant disclosure preferably includes less than 4 wt. %, less than 3 wt. %, less than 2 wt. %, less than 1 wt. %, less than 0.5 wt. % of water and monoalcohols having from 1 to 6 carbon atoms.

Nonlimiting examples of monoalcohols having from 1 to 6 carbon atoms include methyl alcohol, ethyl alcohol, n-propyl alcohol, isopropyl alcohol, n-butyl alcohol, sec-butyl alcohol, isobutyl alcohol, t-butyl alcohol, n-pentyl alcohol, isopentyl alcohol, neopentyl alcohol, cyclopentyl alcohol, n-hexanol, cyclohexyl alcohol, and combination thereof. In various embodiments, the compositions are free or essentially free from one or more (or all) of the monoalcohols set forth above.

In various embodiments, the hair coloring compositions include less than 4 wt. %, less than 3 wt. %, less than 2 wt. %, less than 1 wt. %, less than 0.5 wt. %, or less than 0.1 wt. % of the one or more monoalcohols having from 1 to 6 carbon atoms, provided that the total amount of water and the one or more monoalcohols is less than 5 wt. %. In various embodiments, the hair coloring compositions include less than 4 wt. %, less than 3 wt. %, less than 2 wt. %, less than 1 wt. %, less than 0.5 wt. %, or less than 0.1 wt. % of the water, provided that the total amount of water and the one or more monoalcohols is less than 5 wt. %. Furthermore, the compositions may be free or essentially free from water and/or monoalcohols having from 1 to 6 carbon atoms.

(g) Emollients

In various embodiments, the compositions of the instant disclosure include one or more emollients. Nonetheless, in other embodiments, one or more emollients are not present, i.e., the composition is free or essentially free from emollients. Nonlimiting examples of emollients include fatty esters, fatty ethers, propylene glycol fatty acid esters, fatty carbonate esters, and a combination thereof. In a preferred embodiment, the one or more emollients is selected from dicaprylyl carbonate, dicaprylyl ether, propylene glycol dicaprylate/dicaprate, and a combination thereof.

i. Fatty Esters

Non-limiting examples of fatty esters include fatty esters from a $C_6$-$C_{32}$ fatty acid and/or a $C_6$-$C_{32}$ fatty alcohol. These esters may be esters of saturated or unsaturated, linear or branched $C_1$-$C_{26}$ aliphatic mono or polyacids and of saturated or unsaturated, linear or branched $C_1$-$C_{26}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In various embodiments, the hair coloring compositions include cetyl esters. Cetyl esters is a mixture of the following esters of saturated fatty acids and fatty alcohols: cetyl palmitate, cetyl stearate, myristyl myristate, myristyl stearate, cetyl myristate, and stearyl stearate.

Mention is made of esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate, diisopropyl sebacate, diisopropyl adipate, di-n-propyl adipate, triisopropyl citrate, glyceryl trilactate, glyceryl trioctanoate, neopentyl glycol diheptanoate, and diethylene glycol diisononanoate.

Nonlimiting examples of liquid esters (ester oils) or liquid fatty esters that may be mentioned include, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, and shea butter oil, and caprylic/capric triglyceride.

Nonlimiting examples of solid fatty esters include solid esters obtained from $C_9$-$C_{26}$ fatty acids and from $C_9$-$C_{26}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

In a preferred embodiment, at least one of the one or more emollients is selected from cetyl esters, purcellin oil (cetearyl octanoate), isopropyl myristate, isopropyl palmitate, C12-C15 alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, pentaerythritol esters, diisostearyl malate, neopentyl glycol dioctanoate, dibutyl sebacate, di-C12-13 alkyl malate, dicetearyl dimer dilinoleate, dicetyl adipate, diisocetyl adipate, diisononyl adipate, diisostearyl dimer dilinoleate, diisostearyl fumarate, and a combination thereof.

ii. Fatty Ethers

Nonlimiting examples of fatty ethers include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a combination thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and combinations thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and combinations thereof. In yet another embodiment, at least one of the emollients is a fatty ether selected from stearyl ether, dicaprylyl ether, dicetyl ether distearyl ether, dodecyl ether, dilauryl ether, dimyristyl ether, diisononyl ether, or a combination thereof.

In a preferred embodiment, the composition includes dicaprylyl ether, and optionally one or more additional emollients.

iii. Propylene Glycol Fatty Acid Esters

Nonlimiting examples of propylene glycol fatty acid esters include propylene glycol esters of medium chain fatty acids (fatty acids having from 6 to 12 carbon atoms), such as propylene glycol dicaprylate/dicaprate, propylene glycol dipelargonate, and propylene glycol dilaurate. A preferred propylene glycol fatty acid ester is propylene glycol dicaprylate/dicaprate. The term "propylene glycol dicaprylate/dicaprate" is understood by those in the art to refer to a combination containing propylene glycol dicaprylate, propylene glycol dicaprylate-caprate, and propylene glycol dicaprate, which may vary in the ratio of these components. An example of a commercially available form of propylene glycol dicaprylate/dicaprate is CAPTEX® 200, available from the Abitec Corp. (Columbus, OH, USA).

In a preferred embodiment, the compositions include propylene glycol dicaprylate/dicaprate, and optionally, one or more additional emollients.

iv. Fatty Carbonate Esters

Nonlimiting examples of fatty carbonate esters include dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a combination thereof.

In a preferred embodiment, the compositions include dicaprylyl carbonate, and optionally one or more additional emollients.

The total amount of the one or more emollients will vary. Nonetheless, in various embodiments, the total amount of the one or more emollients, if present, is from about 0.1 to about 10 wt. %, based on the total weight of the compositions. In further embodiments, the total weight of the one or more emollients is from about 0.1 to about 8 wt. %, about 0.1 to about 5 wt. %, about 0.1 to about 4 wt. %, about 0.1 to about 3 wt. %, about 0.1 to about 2 wt. %, about 0.5 to about 10 wt. %, about 0.5 to about 8 wt. %, about 0.5 to about 5 wt. %, about 0.5 to about 4 wt. %, about 0.5 to about 3 wt. %, about 0.5 to about 2 wt. %, about 1 to about 10 wt. %, about 1 to about 8 wt. %, about 1 to about 5 wt. %, about 1 to about 4 wt. %, about 1 to about 3 wt. %, or about 1 to about 2 wt. %, including ranges and sub-ranges therebetween, based on the total weight of the composition.

Fatty Acids

In various embodiments, the hair coloring compositions of the instant disclosure include one or more fatty acids. However, in other embodiments, the compositions do not include fatty acids, i.e., the compositions are free or essentially free from fatty acids. A fatty acid is a carboxylic acid with an aliphatic chain, for example, of 8 to 30 carbon atoms, preferably 8 to 28 carbon atoms, more preferably from 12 to 26 carbon atoms, which is either saturated or unsaturated, and branched or unbranched. Most naturally occurring fatty acids have an unbranched chain of an even number of carbon atoms, from 6 to 28. In some instances, naturally occurring fatty acids are preferred.

Nonlimiting examples of fatty acids include caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof.

In a preferred embodiment, the one or more fatty acids are selected from non-linear fatty acids. The term "non-linear fatty acids" as used in the instant disclosure refers to unsaturated fatty acid and/or branched fatty acids. Unsaturated fatty acid carbon chains contain one or more double bonds with a terminal carboxylic group (—COOH). A fatty acid with a single double bond is termed "monounsaturated fatty acid," and fatty acids with more than one double bond are termed "polyunsaturated fatty acids." Nonlimiting examples of unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof. In a preferred embodiment, the one or more fatty acids includes oleic acid, and optionally one or more additional fatty acids.

Nonlimiting examples of branched fatty acids include isostearic acid.

The total amount of the one or more fatty acids in the hair coloring compositions, if present, will vary. Nonetheless, in various embodiments, the total amount of the one or more fatty acids is from about 0.01 to about 10 wt. %, based on the total weight of the compositions. In further embodiments, the total amount of the one or more fatty acids is from about 0.01 to about 8 wt. %, about 0.01 to about 5 wt. %, about 0.01 to about 3 wt. %, about 0.05 to about 10 wt. %, about 0.05 to about 8 wt. %, about 0.05 to about 5 wt. %, about 0.05 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, about 0.5 to about 3 wt. %, or about 0.5 to about 2 wt. %, including ranges and sub-ranges therebetween, based on the total weight of the composition.

Thickening Polymers

In certain embodiments, the hair coloring compositions of the instant disclosure include one or more thickening polymers. However, in other embodiments, the hair coloring compositions do not include thickening polymers, i.e., the composition is free or essentially free from thickening polymers. When included, in various embodiments, the one or more thickening polymers may be selected from nonionic thickening polymers, cationic thickening polymers, and a combination thereof.

Nonlimiting examples of nonionic thickening polymers, polyacrylate polymers, polyacrylamide polymers, polysaccharides, gums (e.g. guar gums), and a combination thereof. The cationic thickening polymers include cationic polymers having quaternary amine group or a quaternary ammonium group. In a preferred embodiment, the composition includes one or more cationic thickening polymers selected from polyquaternium-10, polyquaternium-67, and a combination thereof, preferably polyquaternium-67.

The total amount of the one or more thickening polymers in the hair coloring compositions, if present, will vary. Nonetheless, in various embodiments, the total amount of the one or more thickening polymers is from about 0.01 to about 5 wt. %, based on the total weight of the composition. In further embodiments, the total amount of the one or more thickening polymers is from about 0.01 to about 4 wt. %, about 0.01 to about 3 wt. %, about 0.01 to about 2 wt. %, about 0.01 to about 1 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.1 to about 5 wt. %, about 0.1 to about 4 wt. %, about 0.1 to about 3 wt. %, about 0.1 to about 2 wt. %, or about 0.1 to about 1 wt. %, including ranges and sub-ranges therebetween, based on the total weight of the composition.

i. Nonionic Thickening Polymers

In various embodiments, the compositions of the present disclosure include one or more nonionic thickening polymers. Nonlimiting examples of nonionic thickening polymers include methyl hydroxypropyl cellulose, Gellan Gum (Kelcogel from CP Kelco), polysaccharide, gum, hydroxyl propyl cellulose (Methocel from Dow/Amerchol), hydroxyl propyl methyl cellulose (Klucel from Hercules), hydroxyl ethyl cellulose, polyalkylene glycols, and combinations thereof. Particularly useful nonionic polymers include polysaccharide gum, hydroxyl propyl cellulose, hydroxyl propyl methyl cellulose, or combinations thereof.

The one or more nonionic thickening polymers may include polysaccharides, especially polysaccharides selected from modified or unmodified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcellulose loses, hydroxyalkylcelluloses, ethylhydroxyethylcelluloses), xylans including glucuronoxylans and arabinoxylans, glucans including xyloglucans, arabans, galactans including arabinogalactans, chitin, agars, locust bean gums, mannans including glucomannans and galactomannans such as guar gums and nonionic derivatives thereof (hydroxypropyl guar), and combinations thereof.

In a preferred embodiment, the one or more nonionic thickening agents are selected from polyacrylate polymers, polyacrylamide polymers, polysaccharides, gums, and a combination thereof, more preferably selected from polysaccharides, gums, and combinations thereof, and even more preferably selected from guar gums, modified guar gums such as hydroxypropyl guar, and celluloses, for example, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and combinations thereof. In some instances, the cellulose is selected from water soluble cellulose derivatives (for example, methyl cellulose, methylhydroxypropyl cellulose, hydroxyethyl cellulose, hydroxypropyl cellulose, cellulose sulfate sodium salt), and combinations thereof. Furthermore, in some instance, the cellulose is preferably hydroxypropylcellulose (HPC).

The total amount of the one or more nonionic thickening polymers, if present, will vary. Nonetheless, in various embodiments, the total amount of the one or more nonionic thickening polymers is from about 0.01 to about 5 wt. %, based on the total weight of the composition. In further embodiments, the total amount of the one or more thickening polymers is from about 0.01 to about 4 wt. %, about 0.01 to about 3 wt. %, about 0.01 to about 2 wt. %, about 0.01 to about 1 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.1 to about 5 wt. %, about 0.1 to about 4 wt. %, about 0.1 to about 3 wt. %, about 0.1 to about 2 wt. %, or about 0.1 to about 1 wt. %, including ranges and sub-ranges therebetween, based on the total weight of the composition.

ii. Cationic Thickening Polymers

In various embodiments, suitable cationic thickening polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species. Anionic counterions can be used in association with the cationic thickening polymers. Non limiting examples of such counterions include halides (e.g., chloride, fluoride, bromide, iodide), sulfate, and methylsulfate. Non limiting examples of cationic thickening polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference in its entirety. More specifically, in various embodiments, the one or more cationic thickening polymer be selected from copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, or vinyl pyrrolidone.

Nonlimiting examples of cationic protonated amino and quaternary ammonium monomers, for inclusion in the cationic thickening polymers, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Additional nonlimiting examples of useful cationic thickening polymers include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquatemium 6 and Polyquaternium 7, respectively); amphoteric copolymers of acrylic acid including copolymers of acrylic acid and dimethyldiallylammonium chloride (referred to in the industry by CTFA as Polyquatemium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquatemium 47). Preferred cationic substituted monomers are the cationic substituted dialkylaminoalkyl acrylamides, dialkylaminoalkyl methacrylamides, and combinations thereof.

In addition to the above, in certain embodiments, the one or more cationic thickening polymers may be selected from cationic polysaccharide polymers, such as cationic cellulose derivatives and cationic starch derivatives. Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200. Other suitable cationic thickening polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers.

In a preferred embodiment, the one or more cationic thickening agents are selected from cellulose based cationic polymers, in particular, selected from polyquaternium-10, polyquaternium-24, polyquaternium-27, polyquaternium-67, polyquaternium-72, and a combination thereof. In a particularly preferred embodiment, the compositions of the instant disclosure include polyquaternium-67.

The total amount of the one or more cationic thickening polymers, if present, will vary. Nonetheless, in various embodiments, the total amount of the one or more cationic thickening polymers is from about 0.01 to about 5 wt. %, based on the total weight of the composition. In further embodiments, the total amount of the one or more thickening polymers is from about 0.01 to about 4 wt. %, about 0.01 to about 3 wt. %, about 0.01 to about 2 wt. %, about 0.01 to about 1 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.1 to about 5 wt. %, about 0.1 to about 4 wt. %, about 0.1 to about 3 wt. %, about 0.1 to about 2 wt. %, or about 0.1 to about 1 wt. %, including ranges and sub-ranges therebetween, based on the total weight of the composition.

Film Forming Polymers

In various embodiments, the compositions of the instant disclosure include one or more film forming polymers (also referred to as "styling polymers"). Nonetheless, in other embodiments, the compositions do not include film forming polymers, i.e., the compositions are free or essentially free from film forming polymers. Nonlimiting examples of film forming polymers include polyalkyloxazolines; vinyl acetate homopolymers; vinyl acetate copolymers; homopolymers and copolymers of acrylic esters; copolymers of acrylonitrile and a nonionic monomer; styrene homopolymers; styrene copolymers (for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine); polyamides; vinylpyrrolidone homopolymers; copolymer of vinylpyrrolidone and vinyl acetate monomers; vinyllactam homopolymers including and polyvinylcaprolactam; and vinyllactam copolymers, such as poly(vinylpyrrolidone/vinyllactam) copolymer, poly(vinylpyrrolidone/vinyl acetate) copolymers; poly(vinylpyrrolidone/vinyl acetate/vinyl propionate) terpolymers; and a combinations thereof.

In various embodiments at least one of the one or more film forming polymers is selected from homopolymers and copolymers derived from at least one nonionic monomer. Nonionic monomers are, for example, acrylamide, methacrylamide, alkyl- and dialkylacrylamide, alkyl- and dialkylmethacrylamide, alkyl acrylate, alkyl methacrylate, vinylcaprolactone, vinylpyrrolidone, vinyl esters, vinyl alcohol, propylene glycol or ethylene glycol, wherein the alkyl groups of these monomers are preferably $C_1$ to $C_7$ alkyl groups and particularly $C_1$ to $C_3$ alkyl groups. Suitable synthetic, nonionic film forming polymers are, for example, the homopolymers of vinylpyrrolidone and the homopolymers of N-vinylformamide. Other suitable synthetic film-forming nonionic film forming polymers are, for example, the copolymers of vinyl pyrrolidone and vinyl acetate, the terpolymers of vinyl pyrrolidone, vinyl acetate and vinyl propionate, and the polyacrylamides, polyvinyl alcohols or polyethylene glycols with a molecular weight of 800 to 20,000 g/mol.

In a preferred embodiment, at least one of the one or more film forming polymers is selected from copolymer of vinylpyrrolidone and vinyl acetate monomers and/or vinylpyrrolidone homopolymers, for example, VP/VA copolymer (or PVP/VA copolymer), PVP, or a combination thereof. In a preferred embodiment, the one or more film forming polymers are selected from polyvinylpyrrolidone (PVP), polyvinylpyrrolidone/vinyl acetate (VP/VA) copolymer, and a combination thereof.

The total amount of the one or more film forming polymers in the hair coloring compositions, if present, will vary. In various embodiments, the total amount of the one or more film forming polymers is from about 0.01 to about 10 wt. %, based on the total weight of the composition. In further embodiments, the total amount of the one or more film forming polymers is from about 0.01 to about 8 wt. %, about 0.01 to about 5 wt. %, about 0.01 to about 3 wt. %, about 0.01 to about 2 wt. %, about 0.05 to about 10 wt. %, about 0.05 to about 8 wt. %, about 0.05 to about 5 wt. %, about 0.05 to about 3 wt. %, about 0.05 to about 2 wt. %, about 0.1 to about 10 wt. %, about 0.1 to about 8 wt. %, about 0.1 to about 5 wt. %, about 0.1 to about 3 wt. %, about 0.1 to about 2 wt. %, about 0.5 to about 10 wt. %, about 0.5 to about 8 wt. %, about 0.5 to about 5 wt. %, about 0.5 to about 3 wt. %, or about 0.5 to about 2 wt. %, including ranges and sub-ranges therebetween, based on the total amount of the composition.

(h) Miscellaneous Ingredients

The compositions the instant disclosure may optionally include (or optionally exclude) one more miscellaneous ingredients. Miscellaneous ingredients are ingredients that are compatible with the hair coloring compositions and do not disrupt or materially affect the basic and novel properties of the compositions. Nonlimiting examples of miscellaneous ingredients include preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

In various embodiments, the compositions of the instant disclosure include one or more miscellaneous ingredients selected from preservatives, fragrances, pH adjusters, salts, chelating agents, buffers, composition colorants, fillers (such as talc, calcium carbonate, silica, including hydrated silica), vitamins, botanical extracts, and a combination thereof. For example, the compositions may include silica (or hydrated silica), tocopherol, fragrances, or a combination thereof.

In the context of the instant disclosure, a "composition colorant" is a compound that colors the composition but does not have an appreciable coloring effect on hair. In other words, the composition colorant is included to provide a color to the composition for aesthetic appeal but is not intended to impart coloring properties to hair. As an example, hair styling gels, can be found in a variety of different colors (e.g., light blue, light pink, etc.) yet application of the styling gel to hair does not visibly change the color of the hair.

The total amount of the one or more miscellaneous ingredients, if present, will vary. Nonetheless, in various embodiments, the compositions of the instant disclosure include from about 0.001 to about 10 wt. % of one or more miscellaneous ingredients, based on the total weight of the composition. In further embodiments, the compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, including ranges and sub-ranges therebetween, based on the total weight of the composition.

Further Embodiments

In various embodiments, the compositions of the instant disclosure may optionally include one or more of polyethylene glycols (PEG), anionic surfactants, anionic polymers, silicones including amine functionalized silicones, and combinations thereof. In other embodiments, the compositions of the instant disclosure are free or essentially free from one or more of polyethylene glycols (PEG), anionic surfactants, anionic polymers, silicones including amine functionalized silicones, and combinations thereof.

In various embodiments, the compositions may be free or essentially free from polyurethanes.

In certain embodiments, the compositions include polyethylene glycol, for example, having at least 2, 3, 5, 10, or 100 repeating units. In other embodiments, the compositions of the instant disclosure are free or essentially free from polyethylene glycol, for example, polyethylene glycol having at least 2, 3, 10, or 100 repeating units. If present, the amount of polyethylene glycol may be from about 0.01 to about 10 wt. %, about 0.1 to about 5 wt. %, or about 0.1 to about 3 wt. %, including ranges and sub-ranges therebetween, based on the total weight of the compositions.

In various embodiments, the compositions of the instant disclosure include one or more anionic surfactants. In other embodiments, the compositions do not include anionic surfactants, i.e., the compositions are free or essentially free from anionic surfactants. Anionic surfactants are known in the art. Nonlimiting examples include sulfate surfactants, isethionate surfactants, sarcosinate surfactants, sulfinate surfactants, taurate surfactants, etc. If present, the total amount of the one or more anionic surfactants may be from about 0.01 to about 5 wt. %, about 0.01 to about 3 wt. %, about 0.01 to about 1 wt. %, about 0.1 to about 4 wt. %, or about 0.1 to about 2 wt. %, including ranges and sub-ranges therebetween, based on the total weight of the composition. In other embodiments, the compositions of the instant disclosure are free or essentially free from anionic surfactants.

In various embodiments, the compositions of the instant disclosure include one or more anionic polymers. In the context of the present disclosure, the term "anionic polymers" is understood as meaning those polymers which carry in a protic solvent under standard conditions at least one structural unit having permanently anionic groups, the anionic groups having to be compensated by counterions while maintaining electroneutrality. As contemplated herein, anionic groups are, for example, carboxylate, sulfate, or sulfonate groups. Nonlimiting examples of anionic polymers include anionic polyurethanes, sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and combinations thereof.

In a preferred embodiment, the compositions of the instant disclosure are free or essentially free from anionic polymers. For example, the compositions may be free or essentially free from any one or more of the anionic polymers referenced above. In addition, the compositions of the instant disclosure may be free or essentially free from one or more, or all of the anionic polymers selected from anionic polyurethanes, sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, polystyrene sulfonate salts, carrageenan salts, dextran sulfate salts, polyacrylic acid salts, poly(methacrylic acid) salts, alginic acid salts, carboxymethylcellulose salts, polystyrene sulfonate/polystyrene copolymer salts, polystyrene sulfonate/maleic acid copolymers salt, copolymers thereof and a combination thereof.

In various embodiments, the compositions of the instant disclosure include one or more silicones. In other embodiments, the compositions are free or essentially free from silicones. Nonlimiting examples of silicones include dimethicone, dimethiconol, cyclomethicone, polysilicone-11, phenyl trimethicone, trimethylsilylamodimethicone, and stearoxytrimethylsilane. In a preferred embodiment, the one or more silicones are non-volatile silicon oils. Useful silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates. Other examples of silicone oils that may be mentioned include volatile linear or cyclic silicones, such as those with a viscosity 8 centistokes ($8 \times 10^6$ m2/s) and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or combinations thereof. In various embodiments, the hair coloring compositions include one or more silicone oils chosen from dimethicone, dimethiconol, cyclomethicone, polysilicone-11, phenyl trimethicone, and amodimethicone, and a combination thereof.

In various embodiments, the compositions include one or more amino functionalized silicones. In other embodiments, the compositions do not include one or more amino functionalized silicones, i.e., the compositions are free or essentially free from amino functionalized silicones. Nonlimiting examples of amino functionalized silicones include amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a combination thereof. Amodimethicone is a particularly useful amino functionalized silicone.

Preferred Embodiments

In a preferred embodiment, the hair coloring composition comprises of consists of:
(a) about 0.001 to about 10 wt. %, preferably about 0.01 to about 8 wt. %, more preferably about 0.1 to about 5 wt. % of one or more hair colorants, for example, one or more direct dyes, oxidative dye precursors, couplers, or a combination thereof, preferably one or more directed dyes, for example selected from azo direct dyes, anthraquinone and anthraquinone derivatives, (poly)methine dyes such as cyanins, hemicyanins and styryls, carbonyl dyes, azine dyes, nitro(hetero)aryl dyes, tri(hetero)arylmethane dyes, porphyrin dyes, phthalocyanin dyes, natural direct dyes, or a combination thereof, preferably at least one of the one or more hair colorants is a direct dye, more preferably an anionic direct dye;

(b) about 5 to about 40 wt. %, preferably about 10 to about 30, more preferably about 10 to about 25 wt. % of one or more ketal/acetal of glycerin compounds of Formula (I), as defined throughout the disclosure, preferably isopropylidene glycerol;

(c) about 0.1 to about 10 wt. %, preferably about 0.5 to about 6 wt. %, more preferably about 1 to about 5 wt. % of one or more cationic surfactants, preferably one or more cationic surfactants selected from quaternary ammonium compounds and fatty alkylamines (such as fatty dialkylamines), more preferably selected from cetrimonium chloride, behentrimonium chloride, behentrimonium methosulfate, stearamidopropyl dimethylamine, and a combination thereof;

(d) about 0.1 to about 10, about 0.5 to about 8 wt. %, more preferably about 1 to about 5 of one of more fatty alcohols having from 10 to 24 carbon atoms, preferably one or more fatty alcohols selected from capryl alcohol, pelargonic alcohol, decyl alcohol, undecyl alcohol, lauryl alcohol, tridecyl alcohol, myristyl alcohol, pentadecyl alcohol, cetyl alcohol, palmitoleyl alcohol, isostearyl alcohol, isocetyl alcohol, heptadecyl alcohol, stearyl alcohol, cetearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, and a combination thereof, more preferably one or more fatty alcohols selected from capryl alcohol, decyl alcohol, undecyl alcohol, lauryl alcohol, myristyl alcohol, cetyl alcohol, isostearyl alcohol, isocetyl alcohol, stearyl alcohol, cetearyl alcohol, oleyl alcohol, arachidyl alcohol, behenyl alcohol, and a combination thereof;

(e) one or more polyols having from 2 to 10 carbon atoms, for example, about 20 to about 90 wt. %, more preferably about 40 to about 85 wt. %, even more preferably about 55 to about 85 wt. %, and even more preferably from about 65 to about 80 wt. % of the one or more polyols having from 2 to 10 carbon atoms, preferably selected from ethylene glycol, propylene glycol, butylene glycol, hexylene glycol, pentylene glycol, 1,3-propanediol, diethylene glycol, dipropylene glycol, caprylyl glycol, and glycerin, more preferably, wherein the polyol is propylene glycol;

(f) less than 5 wt. %, preferably less than 3 wt. %, more preferably less than 2 wt. % of water and monoalcohols having from 1 to 6 carbon atoms;

(g) optionally, about 0.1 to about 10 wt. %, preferably about 0.5 to about 8 wt. %, more preferably about 1 to about 6 wt. % of one or more emollients selected from fatty esters, fatty ethers, propylene glycol fatty acid esters, and fatty carbonates, more preferably one or more emollients selected from dicaprylyl carbonate, dicaprylyl ether, propylene glycol dicaprylate/dicaprate, and a combination thereof;

(h) optionally, about 0.01 to about 5 wt. %, preferably about 0.05 to about 4 wt. %, more preferably about 0.1 to about 3 wt. % of one or more thickening polymers, preferably thickening polymers selected from nonionic thickening polymers and cationic thickening polymers, more preferably one or more nonionic thickening polymers selected from polyacrylate polymers, polyacrylamide polymers, polysaccharides, gums, and and/or one or more cationic thickening polymers selected from polyquaterniums;

(i) optionally, one or more film forming polymers, for example, about 0.1 to about 5 wt. %, preferably about 0.5 to about 4 wt. %, more preferably about 0.5 to about 3 wt. % of film forming polymers, preferably one or more film forming polymers selected from homopolymers of vinylpyrrolidone, homopolymers of N-vinylformamide, copolymers of vinyl pyrrolidone and vinyl acetate, and terpolymers of vinyl pyrrolidone, vinyl acetate, and vinyl propionate, polyacrylamides, polyvinyl alcohols, polyethylene glycols more preferably one or more film forming polymers selected from copolymer of vinylpyrrolidone and vinyl acetate monomers and/or vinylpyrrolidone homopolymers, for example, VP/VA copolymer, PVP, and a combination thereof;

(j) optionally, about 0.01 to about 0.1 to about 10, about 0.5 to about 8 wt. %, more preferably about 1 to about 5 of one of more fatty acid, for example, one or more fatty acids selected from caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof, preferably one or more unsaturated fatty acids, more preferably, one or more unsaturated fatty acids selected from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof;

(k) optionally, about 0.01 to about 5 wt. %, preferably about 0.1 to about 5 wt. %, more preferably about 1 to about 5 wt. % of one or more miscellaneous ingredients, preferably one or more miscellaneous ingredients selected from preservatives, fragrances, salts, pH adjusters, composition colorants, silica, antioxidants, flavonoids, vitamins, botanical extracts, proteins, protein hydrolysates and/or isolates, and UV filtering agents;

wherein all weight percentages are based on a total weight of the composition, and wherein the composition is preferably a solubilized, non-emulsified composition.

Viscosity

The compositions of the instant disclosure typically have a viscosity of about 1 mPa·s to about 10,000 mPa·s at 25° C., about 10 to about 7,000 mPa·s, or about 50 to about 2,000 mP·s. The viscosity measurements can be carried out, for example, using a Broooksfield viscometer, Model: DV-//+ Pro (Brookfield Engineering Laboratories, Inc.) at about 5 revolutions per minute (RPM), at ambient room temperature of about 20 to 25° C.; spindle sizes may be selected in accordance with the standard operating recommendations form the manufacturer, ranging from RV spindle No. 1 to No. 4. As noted above, one or more thickening polymers may optionally be included in the compositions, which will increase the viscosity of the compositions. Therefore, in some instances, the viscosity of the compositions may be from about 500 mPa·s to about 10,000 mPa·s at 25° C.

In various embodiments, the composition have a viscosity from about 1 mPa·s to about 1,000 mPa·s, about 10 mPa·s to about 1,000 mPa·s, about 50 mPa·s to about 1,000 mPas, about 100 mPa·s to about 1,000 mPas, about 250 mPa·s to about 1,000 mPas, about 1 mPa·s to about 750 mPa·s, about 10 mPa·s to about 750 mPa·s, about 50 mPa·s to about 750 mPas, about 100 mPa·s to about 750 mPas, about 250 mPa·s to about 750 m Pas.

In various embodiments, the compositions have a viscosity from about 100 mPa·s to about 5,000 mP·s, from about 200 mPa·s to about 5,000 mP·s, from about 400 mPa·s to about 5,000 mP·s, from about 500 mPa·s to about 5,000 mP·s, from about 750 mP·s to about 5,000 mP·s, from about 100 mPa·s to about 3,000 mP·s, from about 200 mPa·s to about 3,000 mP·s, from about 400 mPa·s to about 3,000 mP·s, from about 500 mPa·s to about 3,000 mP·s, or from about 700 mP·s to about 3,000 mP·s.

Methods

The hair coloring compositions are useful for coloring hair for conditioning and/or styling hair. Typically, when the compositions are applied to wet or damp hair, they form a lamellar phase in situ.

The compositions of the instant disclosure are useful for conditioning and/or managing the hair. Therefore, the compositions may be referred to as "hair treatment compositions." In various embodiments, upon application to the hair, the composition has an opaque appearance. In various embodiments, upon application to wet or damp hair, the composition forms a lamellar phase in situ. A "lamellar phase" refers generally to packing of polar-headed long chain nonpolar-tail molecules in an environment of bulk polar liquid (i.e., water from the hair), as sheets of bilayers separated by bulk liquid. The coloring compositions are useful for coloring hair. Such methods include, for example: (i) applying the coloring composition to the hair; (ii) allowing the coloring composition to remain on the hair for a period of time, for example, from about 10 seconds to about 30 minutes; and (iii) rinsing the coloring composition from the hair. The compositions can be applied to the wet or damp hair and may be massaged into the hair, for example, with the hands, and/or spread throughout the hair with a comb or brush. In addition to providing vibrant color to the hair, the methods result in a smoothing and softening of the hair, which reduces frizz, dryness, and unwanted volume.

In addition to the above method steps, various embodiments are directed to methods of treating hair that include additional steps. For example, when the hair coloring compositions include one or more oxidative dye, the methods typically include the application of a composition containing at least one oxidizing agent (e.g., a developer composition). The hair coloring compositions containing one or more oxidative dyes may optionally include one or more direct dyes. The developer composition may be mixed with the hair coloring composition (e.g., in a 1:1 volumetric ratio) and subsequently applied to dry hair or damp hair. Alternatively, the developer composition may be applied directly to dry hair or damp hair before or after the hair coloring composition is applied to the hair. In other words, the developer composition can be applied to dry or damp hair without being previously mixing the developer composition with a hair coloring composition. Although the amount of hair coloring composition to developer composition may be in a volumetric ratio of 1:1, in some instances the ratio of hair coloring composition to developer composition ranges from 1:5 to 5:1, 1:2 to 2:1, or 1.5:1 to 1:1.5. In at least one preferable embodiment, a developer composition that has not been mixed with a hair coloring composition is applied to hair (either dry or damp hair) before a hair coloring composition is applied to the hair.

In addition to coloring the hair, the compositions are useful for conditioning and/or managing the hair. Therefore, the compositions may be referred to as "hair treatment compositions." The compositions can be applied to the wet or damp hair and may be massaged into the hair, for example, with the hands, and/or spread throughout the hair with a comb or brush. This results in a smoothing and softening of the hair, which reduces frizz, dryness, and unwanted volume. The compositions can remain in the hair or can optionally be rinsed from the hair prior to drying and/or styling of the hair.

In various embodiments, the compositions can be used as a leave-on product. The compositions can be applied to wet or damp hair and allowed to remain on the hair indefinitely, i.e., the hair composition is not removed or rinsed from the hair prior to styling the hair.

The methods of treating hair according to the disclosure also include methods according to various routines. For instance, the compositions may be mixed with a shampoo (or conditioner) prior to application to the hair. Alternatively, the composition may be layered on top of (or lathered into) hair to which the shampoo (or conditioner) is already applied. Furthermore, the composition may be applied separate from the shampoo (or conditioner), i.e., applied to the hair after the shampoo (or conditioner) has been rinsed from the hair. In some instances, it is preferable to treat the hair with a composition of the instant disclosure prior to shampooing the hair, e.g., apply the composition to wet or damp hair prior to application of a shampoo to the hair. The hair may additionally (optionally) be treated with a conditioner after shampooing.

Kits

The hair coloring compositions of the instant disclosure may be incorporated into a kit. For example, the kits may include at least one composition according to the instant disclosure and one or more additional compositions, for example, a shampoo, a conditioner, a developer composition (or just "developer"), etc. The various compositions are separately contained in the kits. In some instances, the kits include one or more compositions according the instant disclosure, a shampoo, and/or a conditioner, all of which are separately contained. In various emobodiments, the kits include one or more compositions according to the instant disclosure and a developer composition. Instructions, mixing components, brushes, gloves, measuring tools, etc., may also optionally be included in the kits.

The compositions may be packaged in a variety of different containers, such as, for example, a ready-to-use container. Non-limiting examples of useful packaging include tubes, jars, caps, unit dose packages, and bottles, including squeezable tubes and bottles.

In various embodiments, the compositions of the instant disclosure are packaged as a spray product, which allows a user to apply the compositions to hair by spraying the composition onto the hair. Furthermore, the compositions may be packaged in a spray bottle, which can be a pump spray bottle that is manually actuated, or the spray bottle can be pressurized such that the compositions are dispensed from a pressurized aerosol container. A propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

In some cases, the compositions are used in conjunction with additional hair-treatment compositions in a routine, for example, during an individual's normal showering/bathing routine. The composition may be applied to the hair individually or may be combined with one or more additional compositions. Combining the compositions with one or more additional compositions (e.g., a shampoo, a conditioner, a rinse, etc.) can be useful for eliminating multiple steps from a routine. For instance, the composition may be mixed with a shampoo (or conditioner) prior to application to the hair. In this case, the mixture of the shampoo (or conditioner) and the composition are simultaneously applied to the hair during the cleansing or conditioning process and simultaneously rinsed from the hair. Alternatively, the composition may be layered on top of (or lathered into) hair to which a shampoo (or conditioner) has already been applied or vice versa. In this case, the composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair-treatment composition is also applied to the hair.

When used in conjunction with a shampoo and/or a conditioner, the composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition of the instant disclosure: shampoo/conditioner, etc.).

The compositions of the instant disclosure may be allowed to remain on the hair for a minimum amount of time before being rinsed from the hair, but it is not necessary to allow the composition to remain on the hair. Conveniently, the compositions can be applied and allowed to remain on the hair for a period of time that is typical for regular shampooing and/or conditioning. For example, the composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the composition is not being mixed with another composition prior to application to the hair, the composition may be applied to the hair immediately after or before the hair it treated with another composition (e.g., a shampoo and/or a conditioner). For example, the hair-treatment compositions may be applied to the hair within about 1, 2, 5, 10, or 20 minutes before or after a shampoo and/or a conditioner is applied to the hair.

The compositions of the instant disclosure are unique in their ability to provide hair with improved manageability, long-lasting style and frizz control, and smoothness. Accordingly, the instant disclosure relates to methods for treating hair, for example, for improving the manageability of hair, for imparting lasting style and frizz control, and for imparting smoothness. More specifically, the compositions may be used in methods for conditioning the hair, providing curl definition to the hair, providing frizz control to the hair, improving ease of combability and detangling, and providing smoothness.

Direct Dyes

Examples of suitable direct dyes that may be mentioned include azo direct dyes; anthraquinone and anthraquinone derivatives; (poly)methine dyes such as cyanins, hemicyanins and styryls; carbonyl dyes; azine dyes; nitro(hetero)aryl dyes; tri(hetero)arylmethane dyes; porphyrin dyes; phthalocyanin dyes, and natural direct dyes, alone or as mixtures. The direct dyes may be cationic or anionic.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| Het⁺-C(Rᵃ)=N—N(Rᵇ)—Ar, An⁻ | (Va) |
| Het⁺-N(Rᵃ)—N=C(Rᵇ)—Ar, An⁻ | (V'a) |
| Het⁺-N=N—Ar, An⁻ | (VIa) |
| Ar⁺—N=N—Ar", An⁻ | (VI'a) and |
| Het⁺-N=N—Ar'—N=N—Ar, An⁻ | (VIIa) | in which formulas (Va), (V'a), (VIa), (VI'a) and (VIIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het⁺ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An⁻ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

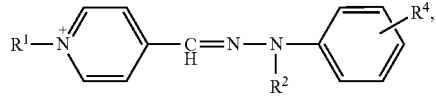
(Va-1)

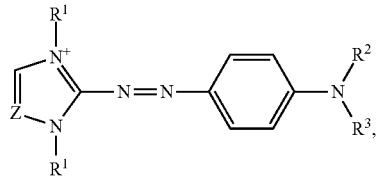
(VIa-1)

formulae (V-1) and (VI-1) with:
- R₁ representing a (C₁-C₄) alkyl group such as methyl;
- R₂ and R₃-, which are identical or different, represent a hydrogen atom or a (C₁-C₄)alkyl group, such as methyl; and
- R₄ represents a hydrogen atom or an electron-donating group such as optionally substituted (C₁-C₈)alkyl, optionally substituted (C₁-C₈)alkoxy, or (di)(C₁-C₈)(alkyl)amino optionally substituted on the alkyl group(s) with a hydroxyl group; particularly, R₄ is a hydrogen atom,
- Z represents a CH group or a nitrogen atom, preferentially CH;
- An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

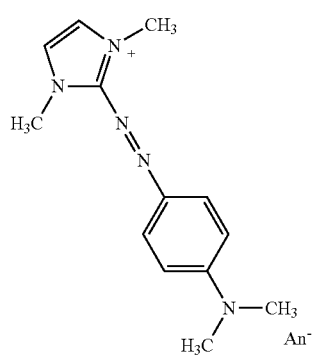
Basic Red 51

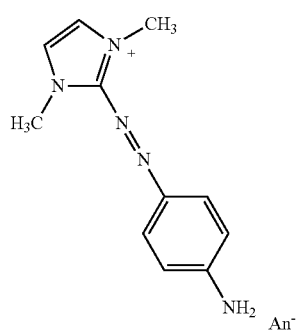
Basic Orange 31

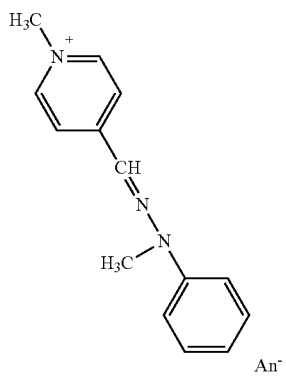
Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2 (Ext Violet 2), D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The total amount of direct dyes in compositions may vary but is typically from about 0.001 to about 10 wt. %, based on the total weight of the composition. In some cases, the total amount of direct dyes in the composition may be from about 0.001 to about 8 wt. %, about 0.001 to about 6 wt. %, about 0.001 to about 5 wt. %, about 0.001 to about 4 wt. %, about 0.001 to about 3 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.1 to about 10 wt. %, about 0.1 to about 8 wt. %, about 0.1 to about 6 wt. %, or about 0.1 to about 5 wt. %, about 0.1 to about 4 wt. %, or about 0.1 to about 3 wt. %, including ranges and sub-ranges therebetween, based on the total weight of the composition.

Oxidative Dye Precursors and Couplers

The hair coloring compositions may include at least one oxidative dye precursors as a colorant. The oxidative dye of the present disclosure may be selected from any type of oxidative dye useful for imparting color to hair. The oxidative dye may also encompass a wide variety of oxidation dye precursors. These include primary dye intermediates and couplers.

i. Primary Dye Intermediates

Examples of primary dye intermediates include ortho or para aminophenols, ortho or para phenylenediamines, double bases, heterocyclic bases, and the acid addition salts thereof.

The para-phenylenediamines which can be used include compounds of the following formula (XIV) and their addition salts with an acid:

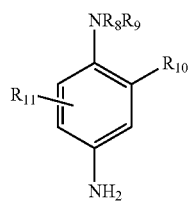

(XIV)

in which:
$R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, a $C_1$-$C_4$ alkyl radical substituted by a nitrogenous group, a phenyl radical or a 4'-aminophenyl radical;
$R_9$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ radical substituted by a nitrogenous group;
$R_8$ and $R_9$ can also form, with the nitrogen atom which carries them, a 5- or 6-membered nitrogenous heterocycle optionally substituted by one or more alkyl, hydroxyl or ureido groups;
$R_{10}$ represents a hydrogen atom, a halogen atom, such as a chlorine atom, a $C_1$-$C_4$ alkyl radical, a sulpho radical, a carboxyl radical, a $C_1$-$C_4$ monohydroxyalkyl radical, a $C_1$-$C_4$ hydroxyalkoxy radical, a $C_1$-$C_4$ acetylaminoalkoxy radical, a $C_1$-$C_4$ mesylaminoalkoxy radical or $C_1$-$C_4$ carbamoylaminoalkoxy radicals;
$R_{11}$ represents a hydrogen atom, a halogen atom or a $C_1$-$C_4$ alkyl radical.

The nitrogenous groups in the above formula (XIV) include amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

The para-phenylenediamines of above formula (XIV) include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine and their addition salts with an acid.

In one embodiment, the para-phenylenediamines of above formula (XIV) include para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid.

The ortho-phenylenediamines include N1-(2-hydroxyethyl)-4-nitro-o-phenylenediamine, 4-methyl-o-phenylenediamine, and 4-nitro-o-phenylenediamine and acid addition salts thereof.

As used herein, the term "double bases" means compounds comprising at least two aromatic nuclei having at least one of amino and hydroxyl groups.

Examples include compounds corresponding to the following formula (XV) and their addition salts with an acid:

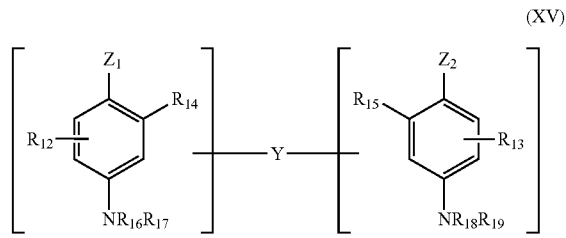

(XV)

in which:
$Z_1$ and $Z_2$, which are identical or different, represent a hydroxyl or —$NH_2$ radical which can be substituted by a $C_1$-$C_4$ alkyl radical or by a connecting arm Y;
the connecting arm Y represents a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or $C_1$-$C_6$ alkoxy radicals;
$R_{12}$ and $R_{13}$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a connecting arm Y;

$R_{14}$, $R_{15}$, $R_{16}$, $R_{17}$, $R_{18}$ and $R_{19}$, which are identical or different, represent a hydrogen atom, a connecting arm Y or a $C_1$-$C_4$ alkyl radical;

it being understood that the compounds of formula (XV) only comprise a single connecting arm Y per molecule.

Nitrogenous groups of the above formula (XV) include amino, mono($C_1$-$C_4$)alkylamino, di($C_1$-$C_4$)alkylamino, tri ($C_1$-$C_4$)alkylamino, monohydroxy($C_1$-$C_4$)alkylamino, imidazolinium and ammonium radicals.

Additional examples of double bases of above formula (XV) include of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis (4-aminophenyl)-tetramethylenediamine, N,N'-bis(β-hydroxyethyl)-N,N'-bis(4-amino-phenyl) tetramethylenediamine, N,N'-bis(4-methylaminophenyl) tetramethylenediamine, N,N'-diethyl-N,N'-bis(4'-amino-3'-methylphenyl)ethylenediamine, 1,8-bis(2,5-diaminophenoxy)-3,5-dioxaoctane and their addition salts with an acid.

In one embodiment the double base is N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid.

The para-aminophenols which can be used include compounds of the following formula (XVI) and their addition salts with an acid:

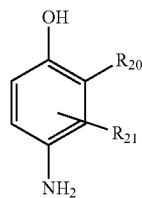

(XVI)

in which:
$R_{20}$ represents a hydrogen atom, a halogen atom, such as fluorine, a $C_1$-$C_4$ alkyl radical, a $C_1$-$C_4$ monohydroxyalkyl radical, a ($C_1$-$C_4$)alkoxy($C_1$-$C_4$) alkyl radical, a $C_1$-$C_4$ aminoalkyl radical or a hydroxy($C_1$-$C_4$)alkylamino-($C_1$-$C_4$)alkyl radical, $R_{21}$ represents a hydrogen atom, a halogen atom, such as fluorine, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical, a $C_1$-$C_4$ cyanoalkyl radical or a ($C_1$-$C_4$)alkoxy($C_1$-$C_4$)alkyl radical.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Heterocyclic bases that can be used as oxidation bases in the methods of coloring keratinous fibers include pyridine derivatives, pyrimidine derivatives, pyrazole derivatives, pyrazolinone derivatives, and the acid addition salts thereof.

Pyridine derivatives include the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Pyrimidine derivatives include the compounds disclosed, for example, in German Patent DE 2 359 399 or Japanese Patents JP 88-169 571 and JP 91-10659 or Patent Application WO 96/15765, such as 2,4,5,6-tetra-aminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a] pyrimidin-3-ylamino)ethanol; 2-[(3-aminopyrazolo[1,5-a] pyrimidin-7-yl)(2-hydroxyethypamino]ethanol; 2-[(7-amino-pyrazolo[1,5-a]pyrimidin-3-yl)(2-hydroxyethyamino) ethanol; 5,6-dimethyl-pyrazolo[1,5-a]pyrimidine-3,7-diamine; 2,6-dimethylpyrazolo[1,5-a]pyrimidine-3,7-diamine; 2,5, N7, N7-tetramethylpyrazolo[1,5-a]pyrimidine-3,7-diamine; 3-amino-5-methyl-7-(imidazolylpropylamino) pyrazolo[1,5-a]pyrimidine; and their addition salts and their tautomeric forms, when there exists a tautomeric equilibrium, and their addition salts with an acid.

Pyrazole and pyrazolinone derivatives include the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1, 3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyppyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, 2-(4,5-diamino-1H-pyrazol-1-yl), $H_2SO_4$, 2,3-diamino-6,7-dihydro-1H,5H-pyrazolo[1,2-z] pyrazol-1-one, 1-methyl-3-phenyl-2-pyrazolinone, and the acid addition salts thereof.

Primary intermediates include p-phenylenediamine, p-aminophenol, o-aminophenol, N,N-bis(β-hydroxyethyl)-p-phenylenediamine, 2,5-diaminotoluene, their salts and combination thereof.

The primary intermediates may be employed in amounts ranging from 0.0001% to 12% by weight, or from 0.0001% to 8.0% by weight, or, from 0.005% to 5% by weight, including ranges and sub-ranges therebetween, based on the total weight of the coloring composition.

ii. Couplers

The hair coloring composition according to the present disclosure may optionally comprise one or more couplers advantageously chosen from those conventionally used in the dyeing or coloring of keratin fibers. The couplers that may be used in the dyeing method disclosed herein include those conventionally used in oxidative methods of coloring keratinous fibers, for example, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1β-hydroxyethylamino-3,4-methylene-dioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene, 2,6-bis(J-hydroxyethylamino) toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and a combination thereof.

Suitable color couplers include, for example, those having the general formula (XVII):

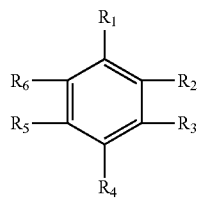

(XVII)

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$-, $R_4$-, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino] benzene, 1-methoxy-2-amino-4-[(beta-hydroxyethyl) amino]benzene, 1-hydroxy-3-(dimethylamino)benzene, 6-methyl-1-hydroxy-3[(beta-hydroxyethypamino]penzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl) amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-aminobenzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and a combination thereof.

Other couplers may be chosen, for example, from 2,4-diamino-1-(β-hydroxyethyloxy)benzene, 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methyl pyrazolo[1,5-a]-benzimidazole, and the acid addition salts thereof.

In one embodiment, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and a combination thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the coloring composition or kits thereof, and preferably from 0.005% to 5% by weight relative to the total weight of the coloring compositions or kits thereof of the present disclosure. The coupler(s), if they are present, each advantageously represent from 0.001% to 10% by weight relative to the total weight of the coloring composition or kits thereof, and preferably from 0.005% to 5% by weight relative to the total weight of the compositions or kits thereof of the present disclosure.

Cationic Surfactants

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and combinations thereof.

In some cases it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include those corresponding to the general formula (III) below:

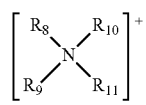

(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula (IV) below:

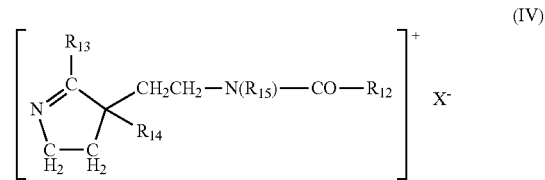

(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a combination of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo;

C. a quaternary diammonium or triammonium salt, in particular of formula (V):

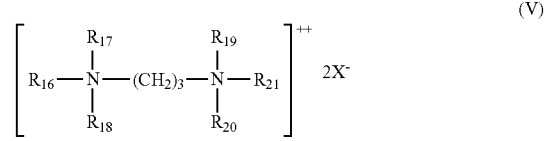

(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N\text{---}(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, for example of the general structure

R4-A-R5-B wherein R4 is a saturated or unsaturated, straight or branched alkyl chain with 8 to 24 C atoms, R5 is a straight or branched alkyl chain with 1 to 4 C atoms, A is selected from:

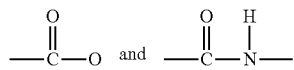

and B is selected from

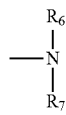

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms,

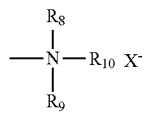

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxyethyldiethyl amine, stearyloxyethylyldimethyl amine, stearyloxyethyl amine, myristyloxypropyl amine, myristyloxypropyldimethyl amine, palmitamidopropyl amine, palm itamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines, preferably, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and combinations thereof. In various embodiments, it is preferably that at least one of the one or more cationic surfactants is a fatty dialkylamine.

Fatty dialkylamines include fatty amidoamine compounds, their salts, and combinations thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine. In a preferred embodiment, the compositions of the instant disclosure include stearamidopropyl dimethylamine, and optionally one or more additional cationic surfactants Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and combinations thereof. In particular, lactic acid or tartaric acid or combinations thereof are useful, especially in combination with fatty dimethylamines such as, for example, stearamidopropyl dimethylamine.

EXAMPLES

Various changes can be made in the above-described compositions and methods without departing from the scope of the invention. Accordingly, it is intended that all disclosure contained in the above description and in the examples given below, shall be interpreted as illustrative and not in a limiting sense.

Example 1

Hair Coloring Compositions

|  |  |  | Comparative | | | Inventive | | | | | |
|---|---|---|---|---|---|---|---|---|---|---|---|
|  |  |  | C wt. % | C-W wt. % | C-S wt. % | A wt. % | B wt. % | C wt. % | D wt. % | E wt. % | F wt. % |
|  | Hair Colorants (Direct Dye) | GREEN 5, RED 40, AND/OR EXT. VIOLET 2 | 0.5 | 0.5 | 0.5 | 0.5 | 0.5 | 0.5 | 0.5 | 0.5 | 0.5 |
| (a) | Formula (I) Compound | ISOPROPYLIDENE GLYCEROL |  | 20 | 20 | 20 | 20 | 20 | 20 | 20 | 20 |
| (b) | Cationic Surfactant | CETRIMONIUM CHLORIDE AND/OR BEHENTRIMONIUM CHLORIDE |  |  |  |  |  |  | 1.2 | 1.2 | 1.2 |
|  |  | STEARAMIDOPROPYL DIMETHYLAMINE |  |  |  | 1.2 | 1.2 | 1.2 |  |  |  |
| (c) | Fatty Alcohol | MYRISTYL ALCOHOL AND/OR CETYL ALCOHOL |  |  |  | 1.5 | 1.5 | 1.5 | 2 | 2 | 2 |
| (d) | Polyol | PROPYLENE GLYCOL |  |  | qs | 74 | 74 | 74 | 74 | 74 | 74 |
| (g) | Emollient | DICAPRYLYL CARBONATE, DICAPRYLYL ETHER, AND/OR PROPYLENE GLYCOL DICAPRYLATE/DICAPRATE |  |  |  | 1.9 | 1.9 | 1.9 | 0.9 | 0.9 | 0.9 |
|  | Thickening Agent | Optional |  |  |  |  |  |  |  |  |  |
|  | Styling Polymer | Optional |  |  |  |  |  |  |  |  |  |
|  | Fatty Acid | Optional |  |  |  |  |  |  |  |  |  |
| (h) |  | Miscellaneous Ingredient |  | ≤5 | ≤5 | ≤5 | ≤5 | ≤5 | ≤5 | ≤5 | ≤5 |
| (f) |  | Water & Lower Monalcohol |  | qs (water) | ≤3 | ≤3 | ≤3 | ≤3 | ≤3 | ≤3 | ≤3 |
|  |  | Lamellar Phase (dilution ratio 1:1, composition:H$_2$O) | NA | No | No | Yes | Yes | Yes | Yes | Yes | Yes |
|  |  | Color Deposition | NA | Very Slight | Very Slight | Yes | Yes | Yes | Yes | Yes | Yes |

\* Compositions A-F differ with respect to the direct dyes included in the compositions. Different direct dyes were used to formulate compositions that impart different colors.

Compositions A-F are inventive compositions. Composition C-W is a comparative composition containing a direct dye in water (Comparative-Water). Composition C-S is a comparative composition containing a direct dye in solvent (Comparative-Solvent). The solvent is a combination of isopropylidene glycerol and propylene glycol. The direct dye used for Composition D (EXT. Violet 2) was used in Compositions C-W and C-S. The first column, designated with a "C" is a control, i.e., an untreated hair swatch. Each composition was uniformally applied to SA 44 bleached hair swatches (1 gram composition per 2.7 gram of swatch). After application to the hair swatches, the hair swatches were rinsed. The resulting color changes (degree of color deposition) were visually evaluated.

Composition C-W and C-S provided very little color change. The swatches were slightly darker but did not exhibit any distinct color change. They were similar in color to the control hair swatch with a darker hue. Inventive Compositions A-F, however, exhibited a pronounced color change and was markedly different from the control swatch and the swatches treated with Compositions C-W and C-S. The swatches treated with the Compositions A-F exhibited distinct blue, green, or red/orange color. Without wishing to be bound by any particular theory, the inventors believe the cationic surfactants are helpful for ensuring the direct dyes adhere to the hair, especially anionic direct dyes which are attracted to the cationic surfactants.

The terms "comprising," "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

A "hair colorant" or "hair coloring agent" is a compound or ingredient included in compositions to intentionally change the color of hair. Nonlimiting examples of coloring agents include direct dyes, oxidative dye precursors, couplers, bleaching agents (e.g., peroxides such as hydrogen peroxide), etc.

A "hair coloring composition" is a composition designed and used to intentionally change the color of hair.

A "composition colorant" is a compound or ingredient that colors the composition but does not have an appreciable coloring effect on hair. In other words, the composition colorant is included to provide a color to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair. Thus, a composition colorant is different from a hair coloring agent. A composition colorant colors the compositions; a hair coloring agent may change the color of the compositions (and often does) but also changes the color of hair The term "rinse-off" as used herein indicates that the composition is used in a context whereby the composition is ultimately rinsed or washed from the treated surface, (e.g. skin, hair, or hard surfaces) either after or during the application of the product. These rinse-off compositions are to be distinguished from compositions referred to a "leave-on" compositions. For example, a rinse-off composition is applied to the hair, optionally allowed to remain on the hair for a short time (e.g., a few second up to about 5, 10, or 15 minutes) and subsequently rinsed from the hair before the hair styled.

The compositions described throughout this disclosure may be a "leave-on" composition. A "leave-on" (also called leave-in) composition refers to a composition that is applied to hair and is not subjected to immediate rinsing and/or washing, for example for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

A "lamellar phase" refers generally to packing of polar-headed long chain nonpolar-tail molecules in an environment of bulk polar liquid (i.e., water from the hair), as sheets of bilayers separated by bulk liquid.

The term "non-linear fatty acids" as used in the instant disclosure refers to unsaturated fatty acid and/or branched fatty acids.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

Throughout the disclosure, the term "a combination thereof" (or a mixture thereof) may be used following a list of elements as shown in the following example where letters A-F represent the elements: "one or more elements selected from the group consisting of A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from the group consisting of A, B, C, D, E, F, and a combination of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a combination thereof," it indicates that that one or more of A, B, C, D, and F may be included, one or more of a salt of A, a salt of B, a salt of C, a salt of D, a salt of E, and a salt of F may be included, or a combination of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

Some of the compounds discussed throughout the disclosure may be in the form of a salt in the composition or added to the composition in the form of a salt (and dissociate in the composition). Thus, all compounds and amounts of compounds relate to both the salt form of the compound and to the disassociated form of the compound. In other words, even if the expression "a salt thereof" is not specifically or expressly stated with respect to ingredients that can form salts or are available as salts, it is understood that the salt form of the compound is included.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the compositions of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping component or ingredient does not represent more than one component. For example, if a polyacrylate falls within the description of a thickening polymer and within the description of film forming polymer, the specifically recited polyacrylate is understood as being only the thickening polymer or only the film forming polymer. A specific polyacrylate cannot simultaneously be construed as both a thickening polymer and a film forming polymer, for example, when the claims set forth both a thickening polymer and a film forming polymer (even though the polyacrylate may function as both a thickening polymer and a film forming polymer). In other words, a single compound or ingredient cannot simultaneously serve as two different components of a claimed composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring composition comprising:
    (a) one or more hair colorants selected from direct dyes, oxidative dye precursors, couplers, and a combination thereof;
    (b) one or more ketal/acetal of glycerin compounds of Formula (I):

wherein $R_1$ and $R_2$ can be the same or different and are independently selected from hydrogen, $C_1$-$C_6$ alkyl, $C_1$-$C_6$ alkenyl, $C_1$-$C_6$ heteroalkyl, $C_1$-$C_6$ heteroalkenyl, aryl, heteroaryl, $C_3$-$C_6$ cycloalkyl, $C_3$-$C_6$ hetero ($C_3$-$C_6$)cycloalkyl, aryl, heteroaryl, optionally substituted; or $R_1$ and $R_2$ may together form a $C_3$-$C_6$ cycloalkyl, $C_3$-$C_6$ heterocycloalkyl, aryl, or heteroaryl, optionally, substituted;
    wherein heteroatoms are selected from N, O or S;
    (c) one or more cationic surfactants;
    (d) one of more fatty alcohols having at least 8 carbon atoms;
    (e) one or more polyols having from 2 to 10 carbon atoms; and
    (f) less than 5 wt. % of water and monoalcohols having from 1 to 6 carbon atoms;
    wherein all weight percentages are based on a total weight of the composition.

2. The composition of claim 1, wherein the composition is a solubilized, non-emulsified composition until applied to wet or damp hair, whereupon the composition forms a lamellar phase in situ.

3. The composition of claim 1, wherein:
    the direct dyes are selected from nitro-phenylenediamines, nitro-aminophenols, azo dyes, anthraquinones, triarylmethane dyes, indophenols, and a combination thereof;
    the oxidative dye precursors are selected from ortho aminophenols, para aminophenols, ortho phenylenediamines, para phenylenediamines, double bases, heterocyclic bases, m-aminophenol, 2,4-diaminophenoxyethanol hcl, toluene-2,5-diamine thioglycerin, p-aminophenol, 2-amino-3 hydroxypyridine, 4-amino-2-hydroxytoluene, acid addition salts thereof, and a combination thereof; and
    the couplers are selected from meta-aminophenols, meta-phenylenediamines and meta-diphenols, naphthols, mono- or polyhydroxylated naphthalene derivatives, heterocyclic couplers, acid addition salts thereof, and a combination thereof.

4. The composition of claim 1, wherein at least one of $R_1$ and $R_2$ is a linear, branched, or cyclic $C_1$-$C_6$ alkyl.

5. The composition of claim 1, wherein $R_1$ and $R_2$ are independently a linear $C_1$-$C_6$ alkyl.

6. The composition of claim 1 comprising:
(b) about 5 to about 95 wt. % of the one or more ketal/acetal of glycerin compounds of Formula (I).

7. The composition of claim 1, wherein the one or more fatty alcohols of (d) are selected from linear fatty alcohols having from 10 to 30 carbon atoms.

8. The composition of claim 1, wherein the one or more fatty alcohols of (d) are selected from capryl alcohol, pelargonic alcohol, decyl alcohol, undecyl alcohol, lauryl alcohol, tridecyl alcohol, myristyl alcohol, pentadecyl alcohol, cetyl alcohol, palmitoleyl alcohol, isostearyl alcohol, isocetyl alcohol, heptadecyl alcohol, stearyl alcohol, cetearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, and a combination thereof.

9. The composition of claim 1 comprising:
(d) about 0.1 to about 10 wt. % of the one or more fatty alcohols.

10. The composition of claim 1, wherein the one or more polyols (e) have two or three hydroxyl groups.

11. The composition of claim 1, wherein the one or more polyols of (e) are selected from ethylene glycol, propylene glycol, butylene glycol, hexylene glycol, pentylene glycol, 1,3-propanediol, diethylene glycol, dipropylene glycol, caprylyl glycol, glycerin, and a combination thereof.

12. The composition of claim 1, further comprising:
(g) one or more emollients.

13. The composition of claim 12, wherein the one or more emollients are selected from fatty esters, fatty ethers, propylene glycol fatty acid esters, fatty carbonates, and a combination thereof.

14. The composition of claim 13 comprising:
(g) about 0.1 to about 10 wt. % of the one or more emollients.

15. The composition of claim 1, further comprising:
(h) one or more miscellaneous ingredients.

16. The composition of claim 15, wherein the one or more miscellaneous ingredients are selected from preservatives, fragrances, salts, pH adjusters, silica, antioxidants, flavonoids, vitamins, botanical extracts, proteins, protein hydrolysates and/or isolates, UV filtering agents, and a combination thereof.

17. A hair coloring composition comprising:
(a) one or more hair colorants selected from direct dyes, oxidative dye precursors, couplers, and a combination thereof;
(b) about 5 to about 30 wt. % of isopropylidene glycerol;
(c) about 0.5 to about 5 wt. % of one or more cationic surfactants;
(d) about 0.5 to about 5 wt. % of one of more fatty alcohols having from 10 to 24 carbon atoms;
(e) about 60 wt. % or more of one or more lower alkyl polyols selected from ethylene glycol, propylene glycol, butylene glycol, hexylene glycol, pentylene glycol, 1,3-propanediol, diethylene glycol, dipropylene glycol, caprylyl glycol, glycerin, and a combination thereof;
(f) less than 5 wt. % of water and monoalcohols having from 1 to 6 carbon atoms;
(g) optionally, about 0.1 to about 5 wt. % of one or more emollients selected from fatty esters, fatty ethers, propylene glycol fatty acid esters, fatty carbonates, and a combination thereof; and
(h) about 0.1 to about 5 wt. % of one or more miscellaneous ingredients selected from preservatives, fragrances, salts, pH adjusters, composition colorants, silica, antioxidants, flavonoids, vitamins, botanical extracts, proteins, protein hydrolysates and/or isolates, UV filtering agents, and a combination thereof;
wherein all weight percentages are based on a total weight of the composition, and
the composition is a solubilized, non-emulsified composition.

18. A method for coloring hair comprising applying to the hair a hair coloring composition comprising:
(a) one or more hair colorants selected from direct dyes, oxidative dye precursor, couplers, and combinations thereof;
(b) one or more ketal/acetal of glycerin compounds of Formula (I):

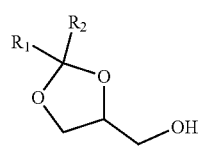

wherein $R_1$ and $R_2$ can be the same or different and are independently selected from hydrogen, $C_1$-$C_6$ alkyl, $C_1$-$C_6$ alkenyl, $C_1$-$C_6$ heteroalkyl, $C_1$-$C_6$ heteroalkenyl, aryl, heteroaryl, $C_3$-$C_6$ cycloalkyl, $C_3$-$C_6$ hetero ($C_3$-$C_6$)cycloalkyl, aryl, heteroaryl, optionally substituted; or $R_1$ and $R_2$ may together form a $C_3$-$C_6$ cycloalkyl, $C_3$-$C_6$ heterocycloalkyl, aryl, or heteroaryl, optionally, substituted;
wherein heteroatoms are selected from N, O or S;
(c) one or more cationic surfactants;
(d) one of more fatty alcohols having at least 8 carbon atoms;
(e) about 50 wt. % or more of one or more lower alkyl polyols having from 2 to 10 carbon atoms; and
(f) less than 5 wt. % of water and monoalcohols having from 1 to 6 carbon atoms;
wherein all weight percentages are based on a total weight of the composition.

19. The method of claim 18, wherein the composition forms a lamellar phase in situ upon application to wet or damp hair.

20. The method of claim 18, further comprising rinsing the composition from the hair after applying the composition to the hair.

* * * * *